United States Patent [19]

Okada

[11] Patent Number: 5,663,214
[45] Date of Patent: Sep. 2, 1997

[54] PHOTOCURING DENTURE BASE LINING MATERIAL

[75] Inventor: Junichi Okada, Tokyo, Japan

[73] Assignee: GC Corporation, Tokyo, Japan

[21] Appl. No.: 629,220

[22] Filed: Apr. 8, 1996

[30] Foreign Application Priority Data

Apr. 17, 1995 [JP] Japan ................... 7-114135

[51] Int. Cl.$^6$ ................... A61C 13/07; A61C 13/23
[52] U.S. Cl. ................... 523/120; 524/533; 524/558; 522/35; 522/908; 433/228.1; 433/168.1; 526/326
[58] Field of Search ................... 523/120; 524/533, 524/558; 522/35, 908; 433/228.1

[56] References Cited

U.S. PATENT DOCUMENTS

| | | | |
|---|---|---|---|
| 3,930,076 | 12/1975 | Kliment | 427/2.29 |
| 4,340,532 | 7/1982 | Lee, Jr. et al. | 524/854 |
| 5,364,890 | 11/1994 | Sakuma et al. | 522/92 |
| 5,436,283 | 7/1995 | Okada et al. | 523/120 |
| 5,500,454 | 3/1996 | Obana et al. | 523/120 |

*Primary Examiner*—Andrew E. C. Merriam
*Attorney, Agent, or Firm*—Oblon, Spivak, McClelland, Maier & Neustadt, P.C.

[57] ABSTRACT

A photocuring denture base lining material is disclosed, comprising:

a powder component comprising a methacrylic acid ester polymer powder and/or a methacrylic acid ester polymer powder having from 0.01 to 5% by weight of a photocuring catalyst compounded therewith; and a liquid component comprising (a) from 10 to 40% by weight of benzyl methacrylate, (b) from 20 to 40% by weight of at least one of compounds represented by the following structural formula (1):

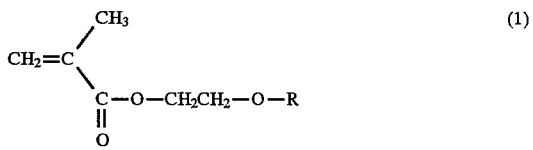

wherein R represents an alkyl group, (c) from 20 to 70% by weight of at least one of methacrylic acid esters having two or three methacryloyl groups in one molecule, and (d) from 0.01 to 5% by weight of a photocuring catalyst. The photocuring denture base lining material of the invention is extremely low in the unpleasant odors and irritation, is superior in the fitness and the operability, and has a high surface hardness after curing.

3 Claims, No Drawings

PHOTOCURING DENTURE BASE LINING MATERIAL

FIELD OF THE INVENTION

The present invention relates to a photocuring denture base lining material which is used for adjustment of the fitness to a denture base by intimately mixing a powder component with a liquid component, building the mixture on the surface of a denture base, setting it in an oral cavity to undergo impression taking of the shape in the oral cavity, and then curing it by photocuring.

BACKGROUND OF THE INVENTION

If a denture the fitness of which has become worse to an oral mucosa is used, not only a person who uses it feels a pain at the time of mastication, but also the denture tends to readily come off. In such a denture, its fitness is amended by using a dental material called a denture base lining material. That is, since when an operation that a denture base lining material is built on the mucosal surface of a denture base and inserted and set in the oral cavity is carried out, the denture base lining material flows corresponding to the shape of the oral cavity and cures, a denture the fitness of which is amended good is obtained. However, since the excessive denture base lining material flows into the cervical and interdental portions remaining in the oral cavity and cures, there was a risk that the denture can not be taken off from the oral cavity.

In order to avoid such a problem, a photocuring denture base lining material has been used. This photocuring denture base lining material does not cure unless it is irradiated with visible light beams. This characteristic is extremely effective for the adjustment operation by a lining material to obtain a denture with superior fitness which hardly comes off. That is, since the shape in the oral cavity changes at the time of mastication or utterance, a denture produced corresponding to the state that a mouth is softly closed sometimes comes off at the time of mastication or utterance. In order to prevent such a problem, it is necessary to adjust the denture base lining material while having a patient masticate or utter. However, since this operation takes a long period of time. In case that a self-curing denture base lining material which polymerizes and cures within a short period of time is used, one can not undergo the adjustment to a satifactory extent and the photocuring denture base lining material is rather convenient.

The composition of the photocuring denture base lining material having such advantages does not differ at all from and is the same as the self-curing denture base lining material except for the type of a catalyst to be used. For this reason, the photocuring denture base lining material has problems common to the self-curing denture base lining material. That is, for conventionally used denture base lining materials, methyl methacrylate and isobutyl methacrylate are used as major components of the liquid, as described in Hirasawa et al., "General Remarks: The present state of commercially available various rebasing materials and as its material science arrangement", in *Ouintessence of Dental Technology*, Vol. 12/1987, December, p. 1475. Since these monomers have irritation against the mucosa and unpleasant odors, a problem that the adjustment of the denture base is very unpleasant to the patient still remains.

Nevertheless, the reasons why the monomers having such defects are still used are as follows. That is, since the denture base lining material must flow into small spaces between the denture base and the mucosa in the oral cavity and cure, the viscosity during building of the denture base should be low. However, since if the viscosity is low for long, the denture base lining material hangs down in the oral cavity and such is difficult for use, and the monomer is set up such that the viscosity rapidly increases. Specifically, if it is set up such that the viscosity reaches 1,500 Pa.sec 8 to 15 minutes after intimate mixing, the dental base lining material is easily used from the clinical viewpoint. Such properties are obtained by the fact that the liquid component of the denture base lining material dissolves therein methacrylic acid ester polymers as major components of the powder. Thus, methyl methacrylate and isobutyl methacrylate which have very high solubility of the methacrylic acid ester polymers and give an appropriate viscosity are used for the denture base lining material.

In recent years, in order to reduce the unpleasant odors and irritation which such materials have, denture base lining materials using neither methyl methacrylate nor isobutyl methacrylate were proposed, a part of which have been made commercially available as a low-irritation lining material. In Japanese Patent Laid-Open Nos.62-178502, 3-74311, 3-206012, 3-206013, 4-29911, 6-48912, and 6-56619, monomers having low irritation and no unpleasant odors are disclosed in place of methyl methacrylate or isobutyl methacrylate. In general, if the number of carbon atoms in the alkyl moiety of a polyalkyl methacrylate is large, the brittle temperature is greatly low as compared with that in methyl methacrylate or isobutyl methacrylate. Since the monomers having low irritation and no unpleasant odors as disclosed in the patents as cited above have a high molecular weight and have a long side chain in terms of polymers as compared with methyl methacrylate and isobutyl methacrylate, the brittle temperature tends to be low. For this reason, if these monomers are applied as the liquid component of the denture base lining material, in order to increase the solubility of the polymers and rapidly bring about an increase in viscosity after intimate mixing with the powder component of the denture base lining material, the monomers must be added in large amounts.

However, denture base lining materials using such a monomer as the major component of the liquid component are soft and are readily scratched. The American Dental Association Specifications No. 17 is concerned with denture base lining materials and defines that the denture base lining materials must have a Knoop hardness of 10 or more. However, it is very hard to meet the requirements in this specification by applying low-irritation monomers having a high molecular weight. If the amount of a monomer to be added having a high molecular weight and having a long side chain in terms of polymers is low, while the Knoop hardness of the denture base lining materials can be increased, the increase in viscosity after intimate mixing of the power component with the liquid component is slow, and hence, such is no longer used. In order to solve such a defect, a method of adding ethanol for the purpose of dissolving the polymers is proposed as disclosed in Japanese Patent Laid-Open No.6-305930. However, the denture base lining materials cured with the ethanol contained therein cause problems such as discoloration. In the light of the above, it has been very difficult to obtain photocuring denture base lining materials having low irritation, bringing about a rapid increase after intimate mixing of the powder component with the liquid component, and having a high surface hardness.

Thus, the present inventor made extensive and intensive investigations in order to obtain a novel denture base lining material which is extremely low in irritation against the mucosa, is substantially free from unpleasant odors, keeps an appropriate viscosity after intimate mixing of the powder component with the liquid component, has an operation down time enough for undergoing precise impression taking of the shape of the mucosal surface in the oral cavity, has a high Knoop hardness after curing by photocuring, and which has no fear of discoloration.

SUMMARY OF THE INVENTION

As a result, it has been found that a photocuring denture base lining material comprising:

a powder component comprising a methacrylic acid ester polymer powder and/or a methacrylic acid ester polymer powder having from 0.01 to 5% by weight of a photocuring catalyst compounded therewith; and a liquid component comprising (a) from 10 to 40% by weight of benzyl methacrylate, (b) from 20 to 40% by weight of at least one of compounds represented by the following structural formula (1):

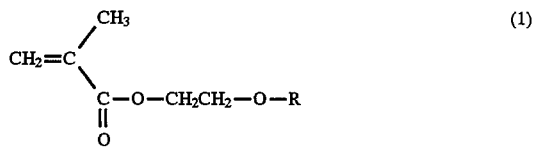

wherein R represents an alkyl group, (c) from 20 to 70% by weight of at least one of methacrylic acid esters having two or three methacryloyl groups in one molecule, and (d) from 0.01 to 5% by weight of a photocuring catalyst, is low in irritation, is free from unpleasant odors, rapidly brings about an increase in viscosity after intimate mixing of the powder component with the liquid component to keep an appropriate viscosity, and provides a cured product having a high surface hardness after irradiation with light beams, thereby achieved the present invention.

DETAILED DESCRIPTION OF THE INVENTION

The photocuring denture base lining material according to the present invention is hereunder explained in more detail.

In the above-referenced structural formula (1), R represents an alkyl group. If the number of carbon atoms of the alkyl group for R is less than 3, the irritation of the monomer appears, whereas if it exceeds 4, the hardness of a denture base lining material of the cured product is low, and the solubility of the polymer is low. For this reason, it is suitable that R represents an alkyl group having 3 or 4 carbon atoms. Specific examples of R are those represented by the following structural formulae:

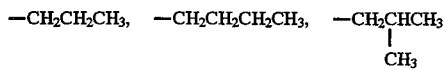

Of these compounds, n-butoxyethyl methacrylate is preferable because it is of low irritation and is superior in the solubility of the polymer.

The liquid component of the photocuring denture base lining material according to the present invention must contain both of the compound represented by the above-referenced structural formula (1) and benzyl methacrylate. Only in case that the both are contained, the characteristics of the photocuring denture base lining material according to the present invention are revealed. That is, in order that a photocuring denture base lining material is prepared from a liquid component consisting of only the compound represented by the above-referenced structural formula (1) and the methacrylic acid ester having two or three methacryloyl groups in one molecule and that it is set up such that the viscosity reaches 1,500 Pa.sec 8 to 15 minutes after intimate mixing, the compound represented by the above-referenced structural formula (1) must be compounded in an amount exceeding 40% by weight. However, if the compounding amount exceeds 40% by weight, the Knoop hardness after photocuring is less than 10 so that the denture base lining material is readily scratched.

In contrast, in case that the liquid component consists of only benzyl methacrylate and the methacrylic acid ester having two or three methacryloyl groups in one molecule, while the Knoop hardness after photocuring is never less than 10, the denture base lining material can not be used because unpleasant odors are present.

It is necessary that the content of benzyl methacrylate is from 10 to 40% by weight. If the content of benzyl methacrylate is less than 10% by weight, the viscosity can not be rapidly increased after intimate mixing of the powder component with the liquid component of the denture base lining material. In contrast, if it exceeds 40% by weight, the cured product is opaque so that the esthetics is inferior. While the smaller the content of benzyl methacrylate, the more superior the esthetics is. Consequently benzyl methacrylate is preferably used in an amount ranging from 10 to 30% by weight from these point of view.

The amount of the monomer represented by the above-described structural formula (1) to be compounded is required to be from 20 to 40% by weight. If the amount of the monomer represented by the structural formula (1) to be compounded is less than 20% by weight, the viscosity can not be rapidly increased after intimate mixing of the powder component with the liquid component of the denture base lining material. In contrast, if it exceeds 40% by weight, the Knoop hardness after photocuring is less than 10 so that the denture base lining material is readily scratched.

Next, at least one of methacrylic acid esters having two or three methacryloyl groups in one molecule is used for the liquid component of the photocuring denture base lining material according to the present invention. While this monomer is low in the solubility of the polymer powder, it is used for the purpose of promoting the curing properties of the denture base lining material. Of such monomers, those having a low viscosity and having no irritation owing to special functional groups and the like are suitable. Examples include 1,3-butanediol dimethacrylate, 1,4-butanediol dimethacrylate, 1,6-hexanediol dimethacrylate, neopentyl glycol dimethacrylate, trimethylolpropane trimethacrylate, and bis(2-methacryloxypolyethoxyphenyl)propane. Of these methacrylic acid esters, 1,6-hexanediol dimethacrylate and neopentyl glycol dimethacrylate are particularly suitable because they are low in the irritation against a mucosa in the oral cavity while they slightly have an ability to dissolve the polymer powders. Since bis(2-methacryloxyethyl) 2,2,4-trimethylhexamethylene dicarbamate, bisphenol A diglycidyl methacrylate, and the like have a high viscosity and readily involve air bubbles at the time of intimate mixing with the powder component, an attention must be paid in use thereof. Such a monomer is compounded in an amount of from 20 to 70% by weight in the photocuring denture base lining material. If the amount of the monomer to be compounded is less than 20% by weight, the effect for promoting the curing properties is low, whereas if it exceeds 70% by weight, the solubility of the polymer powder tends to be lowered. While ethylene glycol dimethacrylate and triethylene glycol dimethacrylate may be used, since these monomers have a bitter taste, they are preferably used in an amount of 10% or less by weight.

In the denture base lining material of the present invention, methacrylic acid ester polymers are used for the powder component. Specific examples include polyethyl methacrylate, polybutyl methacrylate, polyisobutyl methacrylate, ethyl methacrylate-butyl methacrylate copolymers, ethyl methacrylate-methyl methacrylate copolymers, and ethyl methacrylate-isobutyl methacrylate copolymers. Polymers which are suitably used are a polyethyl methacrylate powder as in the conventional type denture base lining materials. Since the polymethyl methacrylate powder are thoroughly soluble only in high-irritation monomers such as methyl methacrylate, it can not be used. Besides, various polymer powders which are readily soluble in plasticizers are enumerated in Japanese Patent Laid-Open No.6-279224. Since these powders are well soluble in monomethacrylates having a high molecular weight, they are applicable to low-irritation denture base lining materials, but an attention must be paid because even after the powder is intimately mixed with the liquid, whereby the viscosity thoroughly increases, sticking sometimes occurs. Furthermore, the polymers which are used have a mean molecular weight of from 100,000 to 1,500,000. Polymers having a mean molecular weight of less than 100,000 are lowered in terms of physical properties so that they are likely broken, whereas those having a mean molecular weight exceeding 1,500,000 are hard to be produced and hence, are not usually used. The polymers which are used have an average grain size of from 20 to 100 μm. Polymers having an average grain size of smaller than 20 μm are likely to induce air bubbles when the powder component is kneaded with the liquid component, whereas those having an average grain size of greater than 100 μm are slow to realize dough-stage and hence, are hard to be used.

In the photocuring denture base lining material according to the present invention, a photocuring catalyst is used for the purpose of achieving the polymerization upon irradition with visible light beams. The photocuring catalyst comprises a photo-sensitizer alone or a combination of a photo-sensitizer with a reducing agent. As the light source, a halogen lamp or a xenon lamp is used, and any of those catalysts which can initiate the radical polymerization of the methacrylic acid ester can be suitably used. Examples of the photosensitizer include α-diketone compounds of such as camphorquinone, polynuclear quinones such as anthraquinone and naphthoquinone, polynuclear quinone derivatives such as 2-methyl-1,4-naphthoquinone and 1,2-benzanthraquinone, chain α-diketone compounds such as benzil and 2,3-pentanedione, benzophenone, benzyl dimethyl ketal, benzoin methyl ether, and benzoin isobutyl ether. Examples of the reducing agent include diethylaminoethyl methacrylate, p-dimethylaminobenzoic acid ethyl ester, p-dimethylaminobenzoic acid isoamyl ester, dimethyl p-toluidine, p-tolyl diethanolamine, benzoyl peroxide, and barbituric acids. Such a photocuring catalyst is usually used in an amount of from 0.01 to 5% by weight in the liquid component. If the amount of the photocuring catalyst to be used is less than 0.01% by weight, the curing rate is so low that the photocuring catalyst is not practically useful, whereas if it exceeds 5% by weight, the curing properties reach the saturated state so that no more improvement in the capacity can be expected. A part of such a photocuring catalyst can be compounded in the powder component. In this case, the photocuring catalyst is compounded in an amount of from 0.01 to 5% by weight in the powder component for the same reasons as described above. Such a photocuring catalyst can also be compounded only in the powder component for the use.

Next, the present invention is hereunder described in more detail with reference to the following Examples. With respect to the Examples and Comparative Examples with compouding rates as described below, the unpleasant odors, irritation, dough-stage time, and Knoop hardness were tested in accordance with the following evaluation methods. The results obtained are shown in Table 1.

(Evaluation for odors and irritation)

In each of the Examples and Comparative Examples, the powder component was intimately mixed with the liquid component, and three minutes after the intimate mixing, the mixture was inserted in the oral cavity of a tester. At this time, the irritation and odors were evaluated in accordance with the following criteria in comparison with a commercially available denture base lining material, "GC Rebaron LC" (a trade mark of GC Corporation).

O: lower

Δ: equal

X: higher

The "GC Rebaron LC" used is the conventional type photocuring denture base lining material using isobutyl methacrylate as the major component of the liquid.

(Dough-strage time)

In each of the Examples and Comparative Examples, the powder component was intimately mixed with the liquid component, the viscosity of the mixture was measured by means of an E-type viscometer "EHD" (manufatured by Tokimec Incorporated). The time required for the mixture to have a viscosity of 1,500 Pa.sec after the initiation of intimate mixing was defined as a dough-stage time. The test was carried out at a number of revolutions of a rotor of 1.0 r.p.m. at 23° C.

(Knoop hardness)

The test was carried out in accordance with the method as described in The American Dental Association Specifications No. 17.

EXAMPLE 1

(Powder component)

Polyethyl methacrylate having a mean molecular weight of 500,000 and an average grain size of 40 μm was compounded with 0.3% by weight of camphorquinone.

(Liquid component)

| | |
|---|---|
| Benzyl methacrylate | 15.0% by weight |
| n-Butoxyethyl methacrylate | 38.0% by weight |
| 1,6-Hexanediol dimethacrylate | 45.5% by weight |
| Dimethylaminoethyl methacrylate | 1.5% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, and the Knoop hardness of its cured product showed a high value as 10.9.

EXAMPLE 2

(Powder component)

Polyethyl methacrylate having a mean molecular weight of 500,000 and an average grain size of 40 μm was compounded with 0.3% by weight of camphorquinone.

(Liquid component)

| | |
|---|---|
| Benzyl methacrylate | 40.0% by weight |
| n-Butoxyethyl methacrylate | 30.0% by weight |
| 1,6-Hexanediol dimethacrylate | 22.8% by weight |
| Ethylene glycol dimethacrylate | 6.0% by weight |
| Dimethylaminobenzoic acid ethyl ester | 1.2% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, and the Knoop hardness of its cured product showed a high value as 11.5.

EXAMPLE 3

(Powder component)

Polyethyl methacrylate having a mean molecular weight of 500,000 and an average grain size of 50 μm was used.

(Liquid component)

| | |
|---|---|
| Benzyl methacrylate | 40.0% by weight |
| n-Butoxyethyl methacrylate | 35.0% by weight |
| 1,6-Hexanediol dimethacrylate | 11.2% by weight |
| Neopentyl glycol dimethacrylate | 11.2% by weight |
| Dimethylaminobenzoic acid ethyl ester | 1.5% by weight |
| 1,2-Benzanthraquinone | 0.1% by weight |
| Benzyl dimethyl ketal | 1.0% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, and the Knoop hardness of its cured product showed a high value as 11.0.

EXAMPLE 4

(Powder component)

Polyethyl methacrylate having a mean molecular weight of 500,000 and an average grain size of 50 μm was compounded with 2.5% by weight of benzoyl peroxide.

(Liquid component)

| | |
|---|---|
| Benzyl methacrylate | 20.0% by weight |
| n-Butoxyethyl methacrylate | 30.0% by weight |
| 1,6-Hexanediol dimethacrylate | 24.4% by weight |
| Neopentyl glycol dimethacrylate | 24.3% by weight |
| Dimethylaminobenzoic acid ethyl ester | 1.0% by weight |
| Camphorquinone | 0.3% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, and the Knoop hardness of its cured product showed a high value as 11.6.

EXAMPLE 5

(Powder component)

Polyethyl methacrylate having a mean molecular weight of 500,000 and an average grain size of 40 μm was compounded with 1.5% by weight of benzoyl peroxide.

(Liquid component)

| | |
|---|---|
| Benzyl methacrylate | 10.0% by weight |
| n-Butoxyethyl methacrylate | 20.0% by weight |
| Neopentyl glycol dimethacrylate | 35.0% by weight |
| Trimethylolpropane trimethacrylate | 32.4% by weight |
| Benzoin methyl ether | 1.0% by weight |
| 1,2-Benzanthraquinone | 0.1% by weight |
| Dimethylaminoethyl methacrylate | 1.5% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, and the Knoop hardness of its cured product showed a high value as 10.6.

EXAMPLE 6

(Powder component)

Polyethyl methacrylate having a mean molecular weight of 500,000 and an average grain size of 40 μm was compounded with 1.0% by weight of 5-butylbarbituric acid.

(Liquid component)

| | |
|---|---|
| Benzyl methacrylate | 10.0% by weight |
| n-Butoxyethyl methacrylate | 20.0% by weight |
| Neopentyl glycol dimethacrylate | 35.0% by weight |
| Trimethylolpropane trimethacrylate | 32.4% by weight |
| Benzoin methyl ether | 1.0% by weight |
| 1,2-Benzanthraquinone | 0.1% by weight |
| Dimethylaminoethyl methacrylate | 1.5% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, and the Knoop hardness of its cured product showed a high value as 10.8.

EXAMPLE 7

(Powder component)

Polyethyl methacrylate having a mean molecular weight of 500,000 and an average grain size of 50 μm was compounded with 2.5% by weight of benzoyl peroxide.

(Liquid component)

| Benzyl methacrylate | 20.0% by weight |
| --- | --- |
| n-Propoxyethyl methacrylate | 30.0% by weight |
| 1,6-Hexanediol dimethacrylate | 24.4% by weight |
| Neopentyl glycol dimethacrylate | 24.3% by weight |
| Dimethylaminobenzoic acid ethyl ester | 1.0% by weight |
| Camphorquinone | 0.3% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, and the Knoop hardness of its cured product showed a high value as 11.8.

COMPARATIVE EXAMPLE 1

(Powder component)

Polyethyl methacrylate having a mean molecular weight of 500,000 and an average grain size of 40 μm was compounded with 2.5% by weight of benzoyl peroxide.

(Liquid component)

| n-Butoxyethyl methacrylate | 40.0% by weight |
| --- | --- |
| Neopentyl glycol dimethacrylate | 40.0% by weight |
| 1,3-Butanediol dimethacrylate | 17.1% by weight |
| Benzoin isobutyl ether | 1.0% by weight |
| 1,2-Benzanthraquinone | 0.1% by weight |
| Camphorquinone | 0.3% by weight |
| Dimethylaminoethyl methacrylate | 1.5% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, but the Knoop hardness of its cured product showed a low value as 9.5.

COMPARATIVE EXAMPLE 2

(Powder component)

Polyethyl methacrylate having a mean molecular weight of 500,000 and an average grain size of 60 μm was used.

(Liquid component)

| Benzyl methacrylate | 40.0% by weight |
| --- | --- |
| 1,6-Hexanediol dimethacrylate | 58.2% by weight |
| 1,2-Benzanthraquinone | 0.1% by weight |
| Camphorquinone | 0.2% by weight |
| Dimethylaminoethyl methacrylate | 1.5% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the irritation but strong in the unpleasant odors. The Knoop hardness of its cured product showed a high value as 11.8.

COMPARATIVE EXAMPLE 3

(Powder component)

Polyethyl methacrylate having a mean molecular weight of 500,000 and an average grain size of 60 μm was used.

(Liquid component)

| Benzyl methacrylate | 50.0% by weight |
| --- | --- |
| n-Butoxyethyl methacrylate | 20.0% by weight |
| 1,6-Hexanediol dimethacrylate | 28.2% by weight |
| Camphorquinone | 0.3% by weight |
| Dimethylaminobenzoic acid isoamyl ester | 1.5% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the irritation but strong in the unpleasant odors. The Knoop hardness of its cured product showed a high value as 11.9.

COMPARATIVE EXAMPLE 4

(Powder component)

Polyethyl methacrylate having a mean molecular weight of 500,000 and an average grain size of 60 μm was compounded with 1.5% by weight of benzoyl peroxide.

(Liquid component)

| Benzyl methacrylate | 30.0% by weight |
| --- | --- |
| n-Butoxyethyl methacrylate | 50.0% by weight |
| 1,6-Hexanediol dimethacrylate | 18.3% by weight |
| Camphorquinone | 0.2% by weight |
| Dimethylaminoethyl methacrylate | 1.5% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, but the Knoop hardness of its cured product showed a low value as 9.1.

COMPARATIVE EXAMPLE 5

(Powder component)

Polyethyl methacrylate having a mean molecular weight of 500,000 and an average grain size of 60 μm was compounded with 1.5% by weight of benzoyl peroxide.

(Liquid component)

| | |
|---|---|
| Benzyl methacrylate | 5.0% by weight |
| n-Butoxyethyl methacrylate | 18.0% by weight |
| Ethylene glycol dimethacrylate | 8.3% by weight |
| 1,6-Hexanediol dimethacrylate | 35.0% by weight |
| Neopentyl glycol dimethacrylate | 32.0% by weight |
| Camphorquinone | 0.2% by weight |
| Dimethylaminoethyl methacrylate | 1.5% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, and the Knoop hardness of its cured product showed a high value as 12.2. But, the dough-stage time was greatly slow as 16 minutes.

COMPARATIVE EXAMPLE 6

(Powder component)

Polyethyl methacrylate having a mean molecular weight of 500,000 and an average grain size of 40 μm was compounded with 0.3% by weight of camphorquinone.

(Liquid component)

| | |
|---|---|
| Methacryloxyethyl propionate | 50.0% by weight |
| 1,6-Hexanediol dimethacrylate | 48.5% by weight |
| Dimethylaminoethyl methacrylate | 1.5% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, but the Knoop hardness of its cured product showed a low value as 9.8.

COMPARATIVE EXAMPLE 7

(Powder component)

Polyethyl methacrylate having a mean molecular weight of 500,000 and an average grain size of 40 μm was used.

(Liquid component)

| | |
|---|---|
| Methoxytriethylene glycol methacrylate | 40.0% by weight |
| 1,6-Hexanediol dimethacrylate | 35.0% by weight |
| Trimethylolpropane trimethacrylate | 23.2% by weight |
| Camphorquinone | 0.3% by weight |
| Dimethylaminoethyl methacrylate | 1.5% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, but the Knoop hardness of its cured product showed a low value as less than 10.

COMPARATIVE EXAMPLE 8

(Powder component)

Polyethyl methacrylate having a mean molecular weight of 500,000 and an average grain size of 40 μm was used.

(Liquid component)

A compound represented by the following structural formula: 40.0% by weight

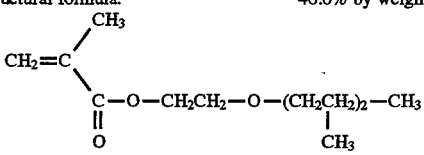

| | |
|---|---|
| 1,6-Hexanediol dimethacrylate | 35.0% by weight |
| Trimethylolpropane trimethacrylate | 23.2% by weight |
| Camphorquinone | 0.3% by weight |
| Dimethylaminoethyl methacrylate | 1.5% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, but the Knoop hardness of its cured product showed a low value as less than 10.

COMPARATIVE EXAMPLE 9

(Powder component)

Polyethyl methacrylate having a mean molecular weight of 500,000 and an average grain size of 40 μm was compounded with 2.0% by weight of benzoyl peroxide.

(Liquid component)

| | |
|---|---|
| Ethoxyethyl methacrylate | 40.0% by weight |
| 1,6-Hexanediol dimethacrylate | 58.2% by weight |
| Camphorquinone | 0.3% by weight |
| Dimethylaminoethyl methacrylate | 1.5% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, but the Knoop hardness of its cured product showed a low value as less than 10.

COMPARATIVE EXAMPLE 10

(Powder component)

Polyethyl methacrylate having a mean molecular weight of 500,000 and an average grain size of 40 μm was compounded with 2.0% by weight of benzoyl peroxide.

(Liquid component)

| | |
|---|---|
| Butoxyethyl methacrylate | 20.0% by weight |
| 1,6-Hexanediol dimethacrylate | 78.2% by weight |
| Dimethyl p-toluidine | 1.5% by weight |
| Camphorquinone | 0.3% by weight |

A photocuring denture base lining material having the composition as described above was prepared by intimately mixing the powder component with the liquid component in a ratio of 1.6 g/1.0 g (powder/liquid) and provided for the tests. The results of the evaluation tests are shown in Table 1.

The resulting denture base lining material was considerably low in the unpleasant odors and irritation, and the Knoop hardness of its cured product showed a high value as 10.3. But, the dough-stage time was greatly slow as 16.5 minutes.

TABLE 1

| | Knoop Hardness (K.H.N.) | Dough-stage Time at 23° C. (min.) | Odors | Irritation |
|---|---|---|---|---|
| Example 1 | 10.9 | 8.5 | ◯ | ◯ |
| Example 2 | 11.5 | 7.6 | ◯ | ◯ |
| Example 3 | 11.0 | 8.2 | ◯ | ◯ |
| Example 4 | 11.6 | 8.9 | ◯ | ◯ |
| Example 5 | 10.6 | 9.5 | ◯ | ◯ |
| Example 6 | 10.8 | 9.8 | ◯ | ◯ |
| Example 7 | 11.8 | 8.0 | ◯ | ◯ |
| Comparative Example 1 | 9.5 | 10.5 | ◯ | ◯ |
| Comparative Example 2 | 11.8 | 9.1 | △ | ◯ |
| Comparative Example 3 | 11.9 | 7.9 | △ | ◯ |
| Comparative Example 4 | 9.1 | 7.8 | ◯ | ◯ |
| Comparative Example 5 | 12.2 | 16.0 | ◯ | ◯ |
| Comparative Example 6 | 9.8 | 8.5 | ◯ | ◯ |
| Comparative Example 7 | 9.7 | 9.8 | ◯ | ◯ |
| Comparative Example 8 | 9.5 | 9.5 | ◯ | ◯ |
| Comparative Example 9 | 9.5 | 9.1 | ◯ | ◯ |
| Comparative Example 10 | 10.3 | 16.5 | ◯ | ◯ |

The photocuring denture base lining material of the present invention is extremely low in irritation against the mucosa, is substantially free from unpleasant odors, rapidly increases in terms of the viscosity after intimate mixing of the powder component with the liquid component to thereby keep an appropriate viscosity, has enough time to take the precise impression of the shape of the mucosal surface in the oral cavity, has a high Knoop hardness after curing by photocuring, is superior in the operability and surface curing properties, and enables one to extremely easily and precisely undergo the adjustment works of fitness of the denture base. The thus obtained denture base is not only superior in the fitness but also has a sufficient strength and durability even after using for a long period of time and is superior in the discoloration resistance. In the light of the above, the photocuring denture base lining material according to the present invention can meet all of the requirements for denture base lining materials, enables patients and dentists to undergo a satisfactory remedy, and hence, greatly contributes to the dental treatment.

While the invention has been described in detail and with reference to specific embodiments thereof, it will be apparent to one skilled in the art that various changes and modifications can be made therein without departing from the spirit and scope thereof.

What is claimed is:

1. A photocuring denture base lining material comprising:

a powder component comprising a methacrylic acid ester polymer powder and/or a methacrylic acid ester polymer powder having from 0.01 to 5% by weight of a photocuring catalyst compounded therewith; and a liquid component comprising (a) from 10 to 40% by weight of benzyl methacrylate, (b) from 20 to 40% by weight of at least one of compounds represented by the following structural formula (1):

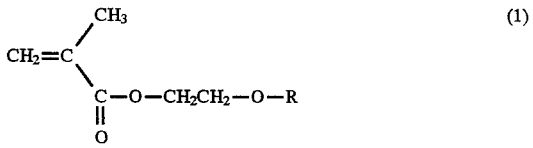

wherein R represents an alkyl group, (c) from 20 to 70% by weight of at least one of methacrylic acid esters having two or three methacryloyl groups in one molecule, and (d) from 0.01 to 5% by weight of a photocuring catalyst.

2. A photocuring denture base lining material as claimed in claim 1, wherein the compound represented by the structural formula (1) is n-butoxyethyl methacrylate.

3. A photocuring denture base lining material as claimed in claim 1 or 2, wherein the methacrylic acid ester having two or three methacryloyl groups in one molecule is either one of 1,6-hexanediol dimethacrylate or neopentyl glycol dimethacrylate or both of 1,6-hexanediol dimethacrylate and neopentyl glycol dimethacrylate.

* * * * *